United States Patent [19]

Strecker

[11] Patent Number: 4,480,332
[45] Date of Patent: Oct. 30, 1984

[54] APPARATUS FOR EXAMINATION BY SCATTERED RADIATION

[75] Inventor: Helmut Strecker, Hamburg, Fed. Rep. of Germany

[73] Assignee: U.S. Philips Corporation, New York, N.Y.

[21] Appl. No.: 374,124

[22] Filed: May 3, 1982

[30] Foreign Application Priority Data

May 23, 1981 [DE] Fed. Rep. of Germany ....... 3120567

[51] Int. Cl.$^3$ .......................................... G01M 23/20
[52] U.S. Cl. .......................................... 378/87; 378/6
[58] Field of Search .................................... 378/6, 87

[56] References Cited

U.S. PATENT DOCUMENTS 3,852,603 12/1974 Muehllehner ...................... 250/369
4,124,804 11/1978 Merell ............................... 378/87
4,380,817 4/1983 Harding ............................. 378/87

Primary Examiner—Craig E. Church
Attorney, Agent, or Firm—Marc D. Schechter

[57] ABSTRACT

The invention relates to an apparatus for imaging a layer of a body to be examined. The body is irradiated by primary radiation, in response to which the layer emits scattered radiation. The apparatus comprises a diaphragm plate which is disposed outside the primary radiation beam. The diaphragm is rotatable about an axis perpendicular to its major surface, and it has at least one aperture which is disposed off of the axis of rotation. A detector or a superposition device is provided for measuring or superimposing the scattered radiation which passes through the diaphragm plate at different aperture settings. The primary radiation is stopped down to form a flat fan-shaped beam. The diaphragm plate is oriented parallel to the fan-shaped beam. Each aperture corresponds to an associated detector, which follows the rotation of the diaphragm plate. The input face of each detector extends parallel to the diaphragm plate. The detector is arranged so as to be rotatable about a detector axis which is perpendicular to an input face and which extends through its center. The detector rotates in a direction opposite to the direction of rotation of the diaphragm plate and with the same angular velocity as this plate.

6 Claims, 4 Drawing Figures

APPARATUS FOR EXAMINATION BY SCATTERED RADIATION

BACKGROUND OF THE INVENTION

The invention relates to an apparatus for imaging a layer to be examined of a body. The body is irradiated by primary radiation, and the layer emits scattered radiation. The apparatus comprises a diaphragm plate which is arranged outside the primary radiation, which is rotatable about an axis perpendicular to its major surface, and which has at least one aperture situated off of the axis of rotation. The apparatus further comprises a detector or a superposition device for measuring or superimposing the scattered radiation which passes through the diaphragm plate at different aperture settings.

Such an apparatus is known from DE-GM 75 41 605. By means of this apparatus, layer-images of the irradiated body can be examined in that initially the scattered radiation, which is emitted by the body and which propagates outside of the primary beam, is detected from different perspectives in order to record sub-images of the body. Subsequently, these sub-images are superimposed by means of a superposition device in such a way that the desired layer images of the body are obtained. The sub-images may, for example, be superimposed by means of the pinhole diaphragm used for recording the images.

As a result of the additional device for superimposing the sub-images, the apparatus has a comparatively intricate construction. Moreover, the contrast of the layer images thus generated is not satisfactory. This is because not only scattered radiation from the body layer to be displayed is measured, but scattered radiation from body areas adjacent to this body layer is also measured.

SUMMARY OF THE INVENTION

It is an object of the invention to provide an apparatus for examination by means of scattered radiation, which in comparison with the known apparatus has a simplified construction and produces improved layer images.

According to the invention this object is achieved by stopping down the primary radiation to form a fan-shaped beam, by orienting the diaphragm plate parallel to the fan-shaped beam, by providing for each aperture an associated detector, whose input face extends parallel to the diaphragm plate, which follows the rotation of the diaphragm plate, and by arranging each detector so as to be rotatable about a detector axis. The detector axis extends perpendicular to its input face and through its center. The detector rotates in a direction opposite to the direction of rotation of the diaphragm plate, and with the same angular velocity as this plate.

The use of a detector which rotates in a direction opposite to that of the diaphragm plate for recording the radiation scattered by the irradiated body layer enables the images of the irradiated body layer to be superimposed simply on each other so that they substantially coincide. If the detector, for example, comprises a radiation-sensitive film, the images on the film may be consecutively exposed. However, the detector may alternatively comprise an electronic image transducer, so that the images consecutively detected by the detector are electronically superimposed and may be displayed as a layer image on, for example, a monitor.

Since the primary radiation which has been stopped down to form a fan beam only irradiates the body layer to be examined, and no body areas adjacent this layer, the layer images formed by means of the present apparatus exhibit a comparatively high contrast. This constrast is only slightly reduced by scattered radiation from body areas adjacent the irradiated body layer, because such scattered radiation is incident at different locations of the detector input faces as a result of the rotation of the diaphragm-plate/detector system. Consequently, such scattered radiation is blurred in the layer image. Moreover, the rotation of the diaphragm-plate/detector system reduces those contrast differences in the layer image which arise because the scattered radiation, issuing from different points of the irradiated body layer traverses paths of different lengths within the body.

In order to obtain a further improvement in the quality of the layer images the body layer to be examined may be irradiated by a plurality of fan-shaped beams, the corresponding sources being, for example, arranged along a circle around the body. This ensures that contrast differences in the layer image caused by attenuation of the primary radiation as it passes through the body are substantially reduced.

The apparatus according to the invention is not only particularly suitable for medical applications, but also for use in the field of nondestructive materials testing. In contrast to medical applications, this demands a high local resolution without imposing limitations on the radiation dose level. Generally, the requirements imposed on the density resolution are also less stringent. When examining the presence of air trapped in castings it is, for example, possible to employ a binary density distribution, so that only comparatively large density steps have to be detected.

DESCRIPTION OF THE PREFERRED EMBODIMENTS

Figure 1:
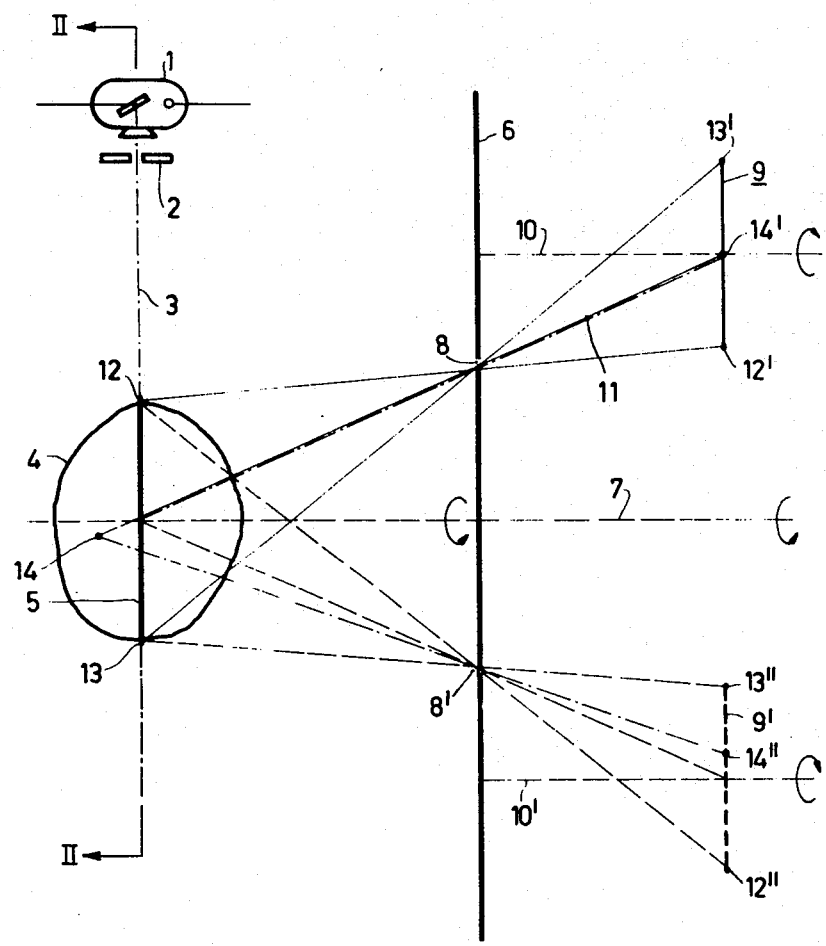
FIG. 1 schematically shows an embodiment of the apparatus for examining a body by scattered radiation according to the invention.

The examining apparatus comprises an X-ray tube 1, whose radiation (primary radiation) is stopped down to form a fan-shaped primary beam 3 by means of a diaphragm 2. The plane of the beam extends perpendicular to the plane of the drawing. The primary beam 3, with which the body 4 is irradiated, serves to define an examination plane 5 within the body 4. The body may be positioned arbitrarily relative to the primary beam 3, producing many possible examination planes.

In order to determine the structure (for example the density distribution or the distribution of scattering coefficients) of the irradiated body layer or examination plane 5, the radiation scattered by this layer is detected. For this purpose, a diaphragm plate 6 is arranged parallel to and opposite the layer 5 to be examined. Diaphragm plate 6 is arranged so as to be rotatable by rotation means 17 (FIG. 2) about an axis 7 which extends perpendicular to the plate and through the center of the layer 5 to be examined.

In one embodiment of the invention, diaphragm plate 6, has only one aperture 8 situated off the axis of rotation 7. The scattered radiation which passes through this aperture 8 is received by a detector 9 associated with this aperture. The detector 9 is mechanically coupled to the diaphragm plate 6 and follows its movement around axis 7.

The detector 9, whose input face extends parallel to the diaphragm plate 6, is also arranged so as to be rotatable by radiation means 18 (FIG. 2); it is rotatable about a detector axis 10 which extends perpendicular to its input face and through its center. The detector axis 10 intersects the input face at the point of intersection of the input face with a straight line 11 as shown in the Figure. Line 11 extends through the aperture 8, and through the intersection of the axis of rotation 7 with the layer 5 to be examined.

The movements of the diaphragm plate 6 and the detector 9 are coordinated in such a way that upon rotation of the diaphragm plate 6/detector 9 system about the axis of rotation 7, the detector 9 simultaneously rotates about the detector axis 10 in a direction opposite to the direction of rotation of the diaphragm plate 6 and with the same angular velocity as the diaphragm plate 6. The scattered-radiation images, which are each recorded with the aperture 8 in different positions relative to the examination layer 5, are illuminated consecutively and in registration on the detector 9, for example an X-ray film.

The reference numerals 8', 9', 10' in FIG. 1 refer to the system comprising the diaphragm plate 6 and the detector 9 in a position which has been rotated through 180° relative to the initial position.

By rotating the system comprising the diaphragm plate 6 and the detector 9 image defects in the relevant scattered-radiation images (which defects are caused by the fact that the scattered radiation originating from different points 12 and 13 in the layer 5 has to cover paths of different lengths within the body 5 and is consequently attenuated differently) are reduced. It is obvious that during rotation the location of the relevant image points 12', 13' and 12'', 13'' respectively relative to the original points 12, 13 is maintained. However, the recording angle and thus the path within the body of the scattered radiation originating from a body point in the layer 5 changes. The undesired attenuation contrasts in the superposition image are blurred by integration of the image intensity, which is effected automatically when X-ray films are used.

By the use of the apparatus according to the invention, scattered radiation originating from points 14 outside the examination layer 5 and caused by multiple scattering is blurred additionally in the superposition image, as illustrated by the image points 14' and 14''. This prevents structures of layers adjacent to the directly irradiated examination layer 5 from being reproduced in the superposition image as a result of multiple scattering.

Figure 2:
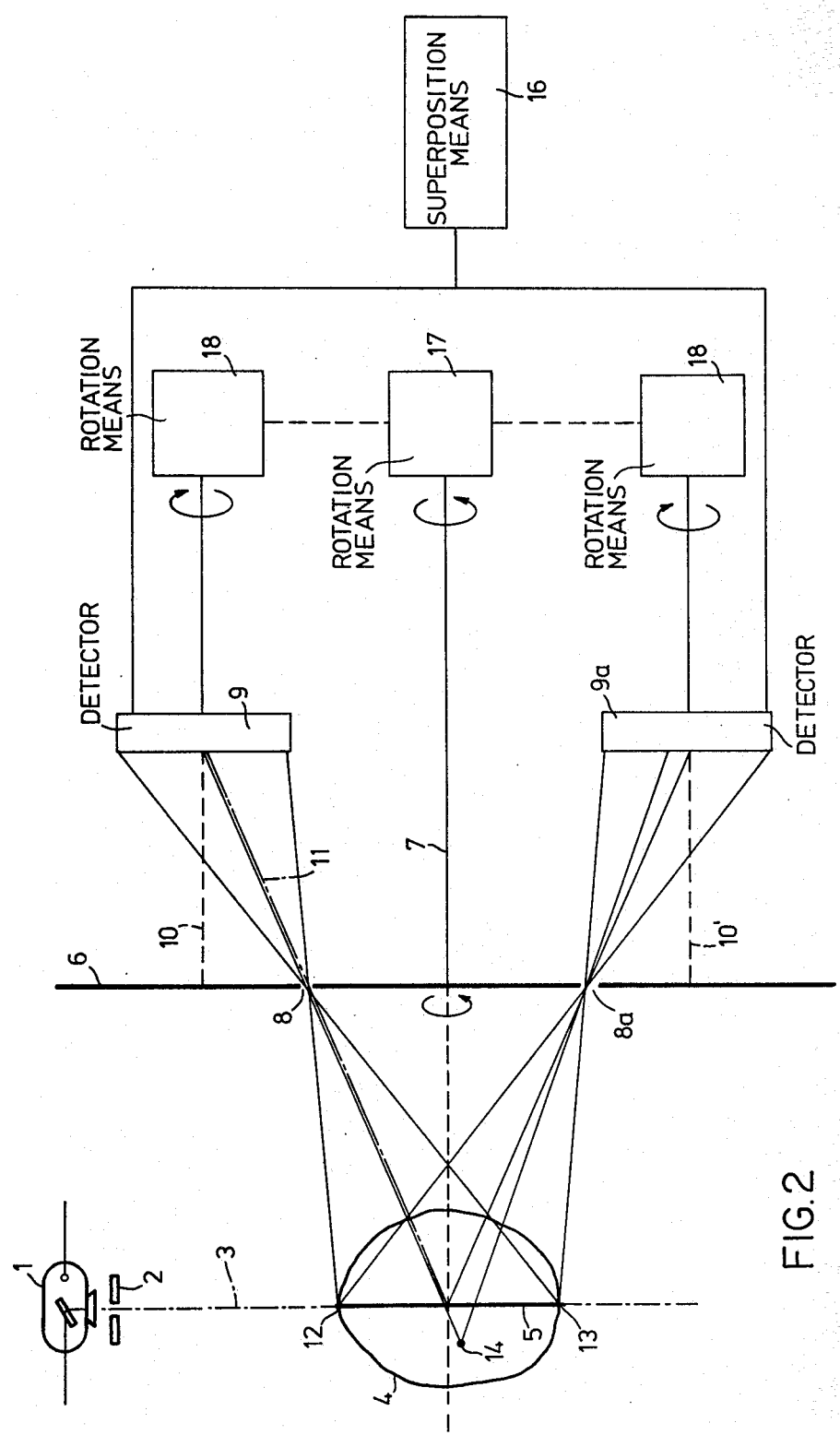
FIG. 2 schematically shows another embodiment of an apparatus according to the invention.

Alternatively, as shown in FIG. 2, the diaphragm plate 6 may comprise a plurality of apertures 8 and 8a, whose associated detectors 9 and 9a are arranged at equal distances from the diaphragm plate 6. For convenience, only two apertures and two detectors as shown. The scattered-radiation images recorded by the detectors are then superimposed by superposition means 16 so as to be in registration. Compared with an apparatus comprising only one detector (in which the system comprising the diaphragm plate 6 and the detector 9 is for example, rotated through 360°), the angle of rotation may then be reduced. Preferably, the apertures and the detectors are arranged to be concentric with the axis of rotation 7 of the diaphragm plate 6.

The scattered radiation images of the individual detectors 9 and 9a may be superimposed electronically so as to be in registration. For this purpose, the detectors may comprise image intensifiers in conjunction with cameras. The cameras may be of the type which are capable of integrating the image intensities incident on their targets (storage cameras) or which are equipped with an image integrator device (For example a real-time video digitizer with summation memory). When X-ray films are used as detectors, optical superposition is possible or electronic superposition after scanning by means of electronic image scanner.

Figure 3:
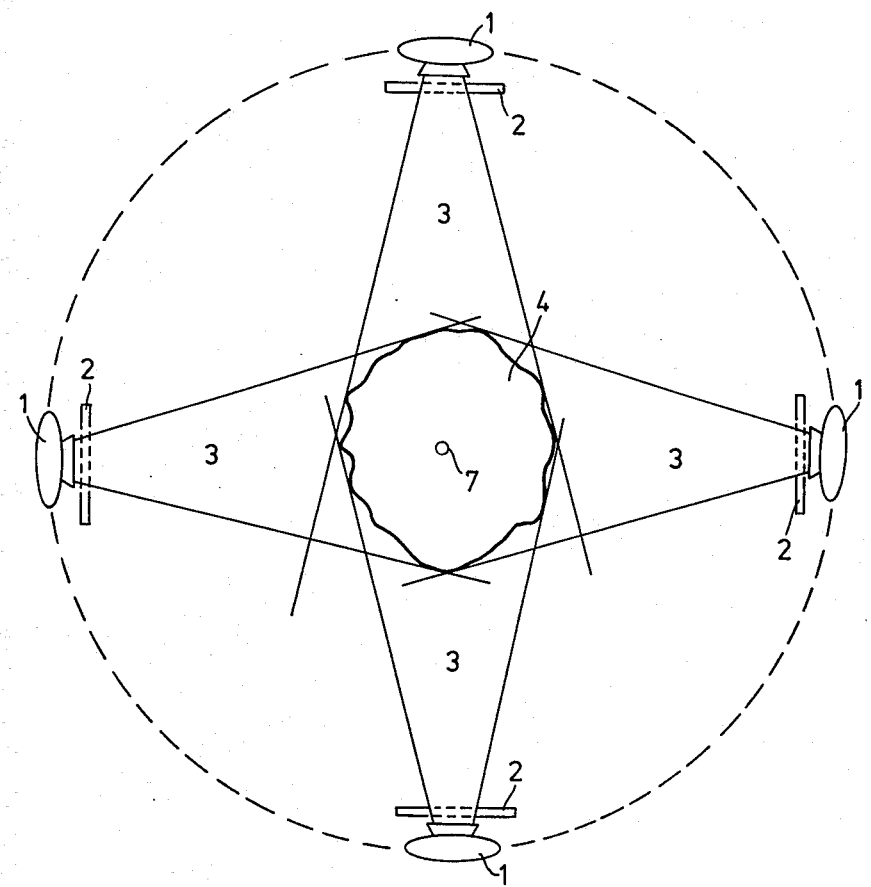
FIG. 3 schematically shows a cross-section along line II—II of FIG. 1.
Figure 4:
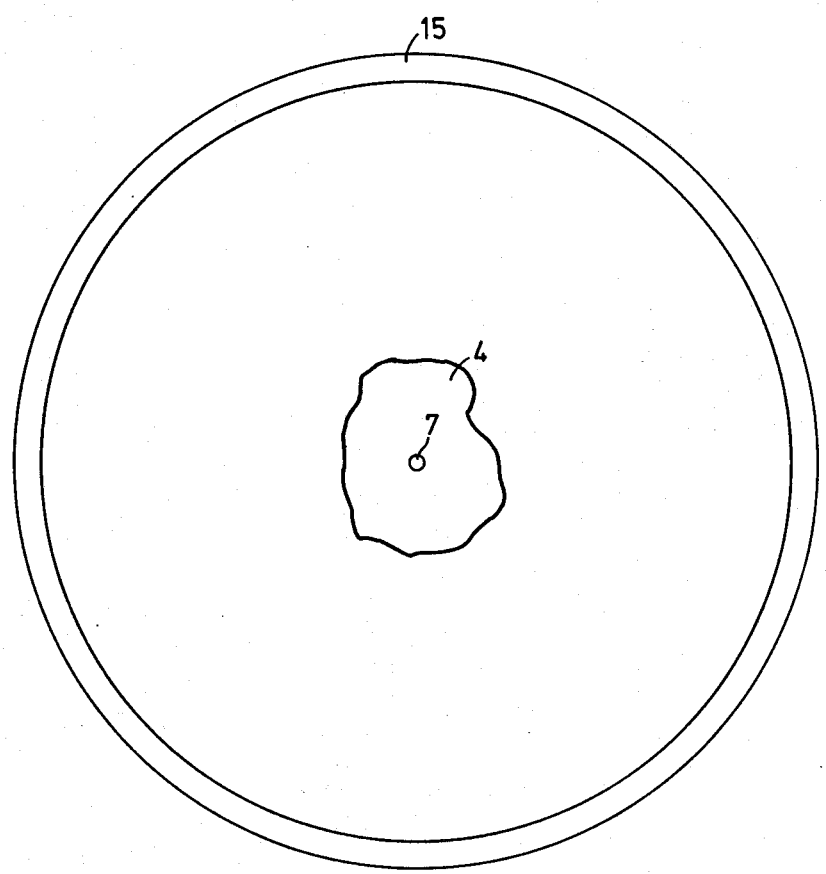
FIG. 4 schematically shows a cross-section through a gamma ray source comprising a ring of isotopic material.

In order to avoid errors in the superposition images as a result of the attenuation of the primary radiation as it passes through the body 4, a plurality of primary radiation sources 1 may be provided for irradiating the examination layer 5 of the body 4, as shown in FIG. 3. For this purpose, the primary radiation sources 1, for example X-ray or gamma ray sources, are arranged around the body 4 along a circle and their radiation is stopped down so as to obtain fan-shaped beams which extend only in the plane 5 to be examined. Furthermore, the primary radiation sources 1 may be arranged so as to be rotatable in the plane of the radiation fans 3 along a circle around the body 4, so that during recording of the scattered-radiation images the positions of the primary radiation sources can be changed and consequently contrast differences in the superposition image as a result of the attenuation of the primary radiation are further reduced. For this purpose a gamma ray source may, for example, comprise a ring 15 of an isotopic material which fully surrounds the body 4, as shown in FIG. 4.

What is claimed is:

1. An apparatus for producing an image of a layer of a body to be examined, said apparatus comprising:
   means for irradiating the body with a flat, fan-shaped beam of radiation to produce scattered radiation by scattering from the body;
   a diaphragm plate having a major surface extending parallel to and outside of the fan-shaped beam, said plate arranged to be rotatable about an axis perpendicular to the major surface, said diaphragm having an aperture therethrough located off of the axis;
   a detector arranged behind the aperture in the diaphragm plate and arranged to rotate with the diaphragm about the diaphragm axis for measuring scattered radiation which passes through the aperture, said detector also being arranged to be rotatable, with the same rotational velocity as the diaphragm plate but with a direction of rotation opposite to that of the diaphragm plate, about a detector axis which is perpendicular to the major surface of the diaphragm plate and which passes through the center of the detector;
   means for rotating the diaphragm plate; and
   means for rotating the detector.

2. An apparatus as claimed in claim 1, characterized in that the detector has an input face arranged parallel to the diaphragm plate.

3. An apparatus as claimed in claim 2, characterized in that:
- the diaphragm plate has a plurality of apertures therethrough;
- the apparatus has a plurality of detectors, one detector associated with each aperture; and
- the detectors each produce pictures, the apparatus further comprising means for superimposing the pictures recorded by the detectors so that the pictures are in registration.

4. An apparatus as claimed in claim 3, characterized in that the apertures are arranged in the diaphragm plate concentrically around the diaphragm axis.

5. An apparatus as claimed in claim 4, characterized in that the apparatus comprises at least two means for irradiating the body with a flat, fan-shaped beam of radiation.

6. An apparatus as claimed in claim 5, characterized in that:
- the means for irradiating the body are arranged on a circle surrounding the body; and
- the circle and the flat, fan-shaped radiation beams are all in one plane.

* * * * *